United States Patent [19]
Wilberscheid

[11] Patent Number: 6,050,966
[45] Date of Patent: Apr. 18, 2000

[54] METHOD FOR STRAIGHTENING A NAIL

[76] Inventor: William A. Wilberscheid, 1919 Coronet, #92, Anaheim, Calif. 92801

[21] Appl. No.: 09/344,188

[22] Filed: Jun. 24, 1999

Related U.S. Application Data

[63] Continuation of application No. 09/137,211, Aug. 20, 1998, abandoned.

[51] Int. Cl.$^7$ ........................................................ A61F 5/11
[52] U.S. Cl. ............................................... 602/31; 132/73
[58] Field of Search ........................... 132/73, 73.5, 75.3, 132/75.4, 75.8, 76.2; 248/300, 205.3; 602/31

[56] References Cited

U.S. PATENT DOCUMENTS

| | | | |
|---|---|---|---|
| 132,872 | 11/1872 | Stedman | 602/31 |
| 884,376 | 4/1908 | Foster | 602/31 |
| 1,219,685 | 3/1917 | Wall | 248/300 |
| 1,451,311 | 4/1923 | Smith | 602/31 |
| 2,202,926 | 6/1940 | Schmidthofer | 602/31 |
| 2,613,667 | 10/1952 | Stanley | 602/31 |
| 3,173,416 | 3/1965 | Rederich | 602/31 |
| 3,409,257 | 11/1968 | Elm | 248/205.3 |
| 3,840,031 | 10/1974 | Walker | 132/160 |
| 4,408,622 | 10/1983 | Meyerhoefer et al. | 132/73 |
| 5,226,433 | 7/1993 | Garcia-Carree | 132/73 |

FOREIGN PATENT DOCUMENTS

| | | | |
|---|---|---|---|
| 23165 | 1/1894 | United Kingdom | 248/205.3 |

*Primary Examiner*—Jeffrey A. Smith
*Assistant Examiner*—Eduardo C. Robert
*Attorney, Agent, or Firm*—Goldstein & Canino

[57] ABSTRACT

A nail straightener, for use on a toenail or fingernail having a nail surface, a nail edge, and located atop a nail bed, comprising a pair of rails extending along the nail surface. The rails each have a hook portion which extends over the nail edge and extends partially beneath the nail, between the nail and nail bed to prevent the nail edge from growing into the nail bed as the nail grows. A bridge connects the rails, and has an adhesive for allowing the nail straightener to be selectively secured to the nail surface, removed and repositioned thereon as the nail grows, and then re-adhered to the nail surface.

3 Claims, 1 Drawing Sheet

METHOD FOR STRAIGHTENING A NAIL

CROSS REFERENCES AND RELATED SUBJECT MATTER

This application is a continuation of patent application Ser. No. 09/137,211, filed in the United States Patent Office on Aug. 20, 1998, now abandoned.

BACKGROUND OF THE INVENTION

The invention relates to a nail straightener. More particularly, the invention relates to a device for guiding the growth of an ingrown toenail or fingernail, to allow it to grow in properly.

Ingrown toenails and fingernails is perhaps one of the most common afflictions resulting from improper grooming. It is especially prevalent with toenails. A combination of improper cutting and poorly fitting shoes can usually result in a toenail growing inward, against the skin. The resulting condition, known commonly as an ingrown toenail, can be extremely painful, making it difficult to walk or even stand.

Frequently, ingrown toenails can require surgery to correct. The surgery can be quite painful, and can require considerable time to recover. In addition, many people neglect the ingrown toenail to the point that it may become infected. Once infected, the ingrown toenail can cause further complications and health hazards.

While these units may be suitable for the particular purpose employed, or for general use, they would not be as suitable for the purposes of the present invention as disclosed hereafter.

SUMMARY OF THE INVENTION

It is an object of the invention to produce a nail straightener which helps straighten an ingrown toenail without requiring surgery. Accordingly, the nail straightener attaches onto a toenail or fingernail and guides the toenail as it grows to ensure that the nail grows in the proper direction. A barrier is provided between the edge of the nail and the skin, to prevent the nail from growing against the skin.

It is another object of the invention to provide a nail straightener which is capable of affixing onto a nail, and is then repositionable as the nail grows to so as to continue to guide the nail as the nail continues to grow. Accordingly, the nail straightener attaches onto the nail with adhesive, so that it may be easily detached therefrom, repositioned, and then reattached.

It is a still further object of the invention that the nail is guided in an unobtrusive way. Accordingly, the guide wraps around the nail opposite the nail bed, to ensure that the nail is guided as it grows.

The invention is a nail straightener, for use on a toenail or fingernail having a nail surface, a nail edge, and located atop a nail bed, comprising a pair of rails extending along the nail surface. The rails each have a hook portion which extends over the nail edge and extends partially beneath the nail, between the nail and nail bed to prevent the nail edge from growing into the nail bed as the nail grows. A bridge connects the rails, and has an adhesive for allowing the nail straightener to be selectively secured to the nail surface, removed and repositioned thereon as the nail grows, and then re-adhered to the nail surface.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
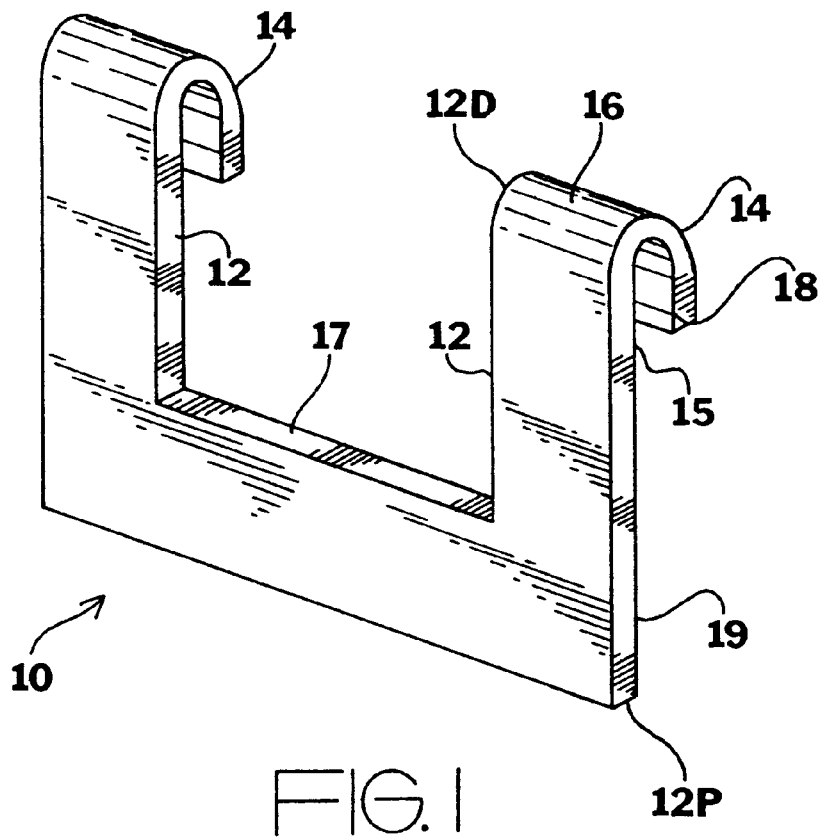
FIG. 1 is a diagrammatic perspective view, illustrating the nail straightener, per se.
Figure 2:
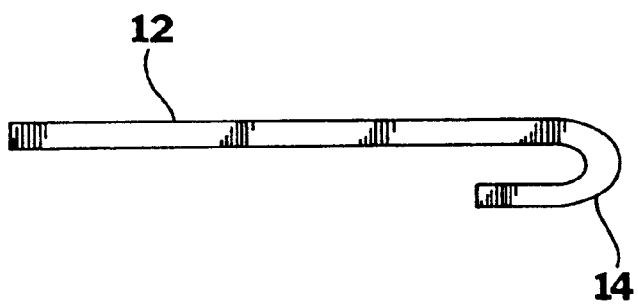
FIG. 2 is a side elevational view thereof.

FIG. 1 illustrates a nail straightener 10. The nail straightener comprises a pair of side rails 12 having a proximal end 12P and a distal end 12D. The side rails 12 having a hook portion 14 at the distal end 12D. However, the side rails 12 are substantially straight from the hook portion 14 to the proximal end 12P. The nail straightener is used upon a nail which is either a toenail or a fingernail. The nail is located atop a nail bed, has a nail surface, and has a nail edge.

The hook portion 14 includes a leading portion 15, an apex 16 and a return 18. The return 18 and leading portion 15 are substantially parallel, but are spaced apart by substantially one thirty second of an inch. In use, the hook portion 14 is placed over the nail edge, with the return 18 extending partially under the nail—between the nail and nail bed. Thus, as the nail grows, the return 18 effectively acts as a barrier between the nail and nail bed, preventing the nail edge from pressing against the skin and then growing inward toward the skin. The hook portion 14 then acts as a guide, continuing to guide the nail edge as the nail grows so that it continues growing parallel to the nail bed until the nail edge reaches the finger tip or even beyond, to prevent the habitual tendency for the nail to once again curve inward toward the nail bed. Once the nail edge reaches the finger tip, the ingrown nail problem is virtually eliminated.

The nail straightener 10 also has a bridge 17 which extends between the rails, perpendicular thereto. The bridge has a bottom surface 19 which preferably has adhesive, so that the bridge 17 adheres to the nail surface to hold the nail straightener 10 in place. The adhesive is preferably selected so that the bridge 17 can be repeatedly adhered to and removed from the nail surface, so that the nail straightener can be repositioned on the nail, as necessary to follow growth of the nail.

In conclusion, herein is presented a nail straightener which effectively attaches to the surface of a fingernail or toenail, and then hooks over the nail edge to create a barrier between the nail edge and skin, to prevent the nail edge from "digging in" to the skin as the nail grows, and thereby training said nail to grow properly.

What is claimed is:

1. A nail straightening method for straightening a nail having a nail surface and a nail edge, said nail selected from a fingernail and a toenail, said nail attached onto a nail bed, using a straightening device having two rails, each having a hook portion having a leading edge, an apex, and a return, the straightening device further having a bridge attaching the two rails opposite the hook portions thereof, comprising the steps of:

placing the hook portion over the nail edge with the return extending partially under the nail;

adhering the bridge to the nail surface;

allowing the nail to grow; and preventing the nail edge from growing against the nail bed by maintaining the nail edge within the hook portion.

2. The nail straightening method as recited in claim 1, wherein the step of allowing the nail to grow is followed by the step of repositioning the bridge to follow growth of the nail.

3. The nail straightening method as recited in claim 2, wherein the bridge has a bottom surface having an adhesive which is selected so that the bridge can be repeatedly adhered and removed from the nail surface as the nail grows.

* * * * *